United States Patent [19]

Peters

[11] Patent Number: 4,675,376

[45] Date of Patent: Jun. 23, 1987

[54] PROCESS FOR THE PREPARATION OF N-ALKYLPHTHALIMIDE AND COPOLYMER DERIVED THEREFROM

[75] Inventor: Edward N. Peters, Lenox, Mass.

[73] Assignee: General Electric Company, Pittsfield, Mass.

[21] Appl. No.: 920,487

[22] Filed: Oct. 17, 1986

Related U.S. Application Data

[62] Division of Ser. No. 553,174, Nov. 18, 1983, Pat. No. 4,623,732.

[51] Int. Cl.[4] .................. C07D 209/48; C07D 403/10

[52] U.S. Cl. ...................................... 528/185; 528/26; 528/125; 528/126; 528/128; 528/172; 528/176

[58] Field of Search ................. 528/185, 26, 125, 126, 528/128, 172, 176

[56] References Cited

U.S. PATENT DOCUMENTS

| | | | |
|---|---|---|---|
| 3,356,648 | 12/1967 | Rogers | 528/353 |
| 3,424,718 | 1/1969 | Angelo | 528/188 |
| 3,649,601 | 4/1972 | Critchley | 528/353 |
| 3,847,867 | 11/1974 | Heath et al. | 528/185 |
| 3,959,350 | 5/1976 | Rogers | 528/185 |
| 3,983,093 | 9/1976 | Williams, III et al. | 528/185 |
| 4,196,277 | 4/1980 | Jones et al. | 528/185 |
| 4,197,396 | 4/1980 | Banucci et al. | 528/185 |
| 4,281,100 | 7/1981 | Takekushi | 528/185 |
| 4,429,102 | 1/1984 | Evans et al. | 528/185 |
| 4,504,605 | 3/1985 | Cooper | 528/185 |
| 4,540,748 | 9/1985 | Matzner et al. | 528/185 |
| 4,612,361 | 9/1986 | Peters | 528/185 |

*Primary Examiner*—John Kight
*Assistant Examiner*—M. L. Moore
*Attorney, Agent, or Firm*—William F. Mufatti; Michael J. Doyle; Martin Barancik

[57] ABSTRACT

A copolymer prepared from a bis-(N-alkyphthalimide), a dianhydride and a diamine, and a process of preparing the copolymer by reacting a bis-(n-alkyphthalimide) with an alkali to form a tetracid, dehydrating the tetracid to a dianhydride and reacting the dianhydride with a diamine under copolymer forming conditions.

6 Claims, No Drawings

PROCESS FOR THE PREPARATION OF N-ALKYLPHTHALIMIDE AND COPOLYMER DERIVED THEREFROM

This is a division of application Ser. No. 553,174, filed Nov. 18, 1983, now U.S. Pat. No. 4,623,732.

This invention is directed to a process for the synthesis of N-alkylphthalimides and copolymers derived therefrom.

BACKGROUND OF THE INVENTION

In the prior art bis(N-alkylphthalimides) have been prepared by coupling nitro-N-alkylphthalimides. This method results in the preparation of intermediates that are gummy solids that are difficult to handle and present purification problems. See U.S. Pat. No. 3,957,862; U.S. Pat. No. 4,017,511; U.S. Pat. No. 3,956,320 and U.S. Pat. No. 3,972,902.

The prior art has recognized that aryl and heteroaryl polyhalides may be coupled by using an anhydrous nickel catalyst. The polyhalides have been converted into polymers due to the presence of at least two halogen atoms in the starting material. Such a process is described in European patent application 79104205.4. Nothing in that application suggests the coupling of monohalide compounds to form a bisimide.

Polyetherimide polymers are known which all are synthesized from biphenol-di (N-methylphthalimide). See for example U.S. Pat. No. 3,983,093. This compound when converted to the dianhydride may be employed to make polyetherimide polymers. The applicant has discovered a novel process for making certain bis(N-alkylphthalimides) that is easily carried out in conventional equipment. The dianhydride derivatives of these compounds may be utilized in making homopolymers and copolymers using diamine coupling agents.

Thus it is a primary object of this invention to provide a novel method for the preparation of certain bis (N-alkylphthalimides) and dianhydrides derived therefrom.

It is also an object of this invention to provide a novel copolymer that is based on the coupling of a dianhydride of certain bis(N-alkylphthalimide) compounds with a dianhydride derivative of certain bisphenols.

DETAILED DESCRIPTION OF THE INVENTION

The process of the invention is directed to the preparation of compounds of formula I:

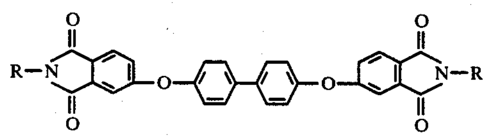

wherein R is lower alkyl of from one to six carbons such as methyl, ethyl, n-propyl, n-hexyl and the like. These compounds are prepared by heating a compound of fromula II:

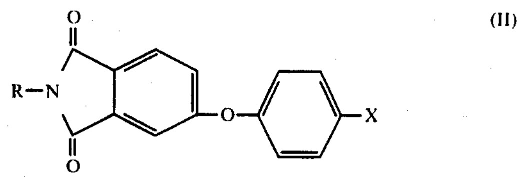

wherein R is the same as set forth hereinabove and X is Br, Cl or I in the presence of a solvent and a catalyst that comprises a nickel compound and a reducing compound.

Suitable solvents for the practice of the invention include saturated aliphatic hydrocarbons and aromatic hydrocarbons such as hexane, pentane, benzene, eylene, etc; ethers such as diethyl ether, tetrahydrofuran etc; dimethylacetamide; dimethyl sulfoxide, dimethylformamide; and the like.

The useful nickel compounds include complexes of nickel and organometallic nickel compounds. These compounds include nickel halides such as nickel chloride, nickel iodide and nickel bromide; nickel sulfate, nickel carbonate, nickel phosphates and the like. Nickel salts of aliphatic organic acids having from 1-20 carbon atoms such as nickel formate, nickel acetate, nickel stearate; nickel complexes such as nickel acetoacetonate and the like.

The amount of nickel that is used is from about 0.005 to about 1.0 and preferably from about 0.01 to about 0.5 moles of nickel per moles of nickel per mole of compound of formula II. An inorganic salt such as an alkali metal bromide may be added to the reaction mixture in an amount of 0.01-500 moles per gram atom of catalyst.

The useful triarylphosphines include triphenylphosphines. The ratio of triarylphosphine to nickel may be from about 0.01 to about 25, and preferably from 1 to 10 moles of triaryl phosphine per mole of nickel.

The reducing metal may be manganese, magnesium or zinc. These reducing metals may be used in a finely divided form at a ratio of 0.5 moles to 1.5 moles per mole of the compound of formula II. Zinc is the preferred reducing metal.

The compounds of formula I may be used to make homopolymers or copolymers if they are first converted to a tetraacid of formula III.

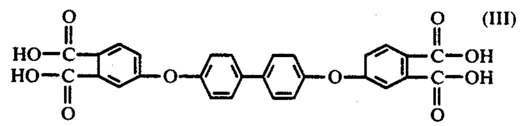

which may be dehydrated to the anhdride of formula IV:

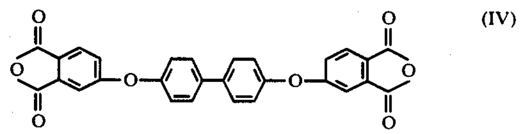

The hompolymers or copolymers are prepared by reaction with a diamine of formula V.

$$H_2N—R^1—NH_2 \quad (V)$$

wherein $R^1$ is a divalent organic radical selected from the class consisting of (a) aromatic hydrocarbon radicals having from 6-20 carbon atoms and halogenated derivatives thereof, (b) alkylene radicals and cycloalkylene radicals having from 2-20 carbon atoms. $C_{(2-8)}$ alkylene terminated polydiorganosiloxane and (c) divalent radicals included by the formula

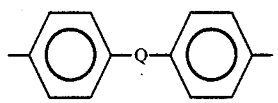

where Q is a member selected from the class consisting of —O—,

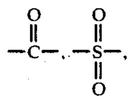

—S—, and $—C_2H_2$, and x is a whole number from 1 to 5 inclusive. In addition, copolymers may be prepared by utilizing from 10-90 mole % of an anhydride of formula IV with 90-10 mole % of a dianhydride of formula VI and a diamine of formula V:

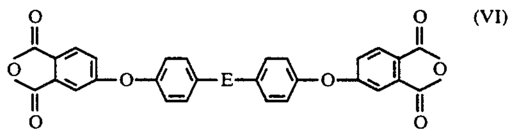

wherein E is selected from phenylene, biphenylene, naphthylene, alkylene or alkylidene. Useful alkylene groups include methylene, ethylene and the like; alkylidene groups include ethylidene and isopropylidene. The preferred group for E is isopropylidene.

The copolymers may be prepared by combining the diamine of formula V with the dianhydrides of formula IV and formula VI in a suitable reactor in the presence of a suitable solvent. The reaction is carried out by heating the reactants in an inert atmosphere such as nitrogen using a suitable means of agitation such as a mechanical stirrer. The water formed by the polymer formation is removed by azeotropic distillation and the polymer may be recovered by precipitation with an antisolvent such as methanol.

The copolymers have repeating units of the formula:

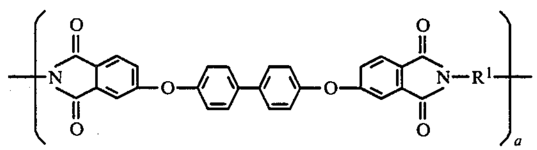

wherein $R^1$ is as defined above; and a represents from 10 to 100 units; and

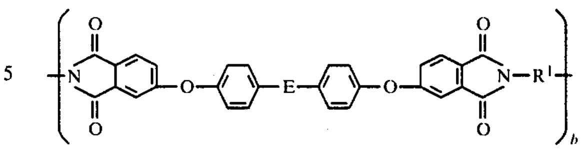

wherein E is selected from the group consisting of phenylene, biphenylene, naphthylene, alkylene or alkylidene and b is from 10 to 100 and $R^1$ is as defined above.

These polymers are thermplastic and may be molded to form useful articles having a high heat distortion temperature. They may be combined with reinforcing fillers and other fillers such as from 1-50% by weight of fibrous glass, wollastonite, clay, talc, mica, carbon fibers, aramid fibers, calcium carbonate and the like. If desired, flame retardant amounts of flame retardant agents such as those described in U.S. Pat. No. 4,020,124, which is incorporated by reference, may be added.

DESCRIPTION OF THE PREFERRED EMBODIMENTS

The following examples illustrate the process of the invention. They are merely illustrative and are not to be construed to limit the invention in any manner whatsoever.

EXAMPLE I

In a 500 ml three-necked flash equipped with a mechanical stirrer, Dean-Stark trap/condenser, nitrogen inlet, and thermometer was added 25.71 grams (0.20 moles) of p-chlorophenol, 100 ml dimethylsulfoxide, and 150 ml of chlorobenzene. After stirring and nitrogen purging the mixture for 30 min., 15.80 grams of aqueous sodium hydroxide (50.62 wt. %; 0.20 moles) was added. The mixture was heated up to 150° C. with the azeotropic removal of the water of reaction. After the removal of water was complete the temperature was lowered to 60° C. and 41.23 grams (0.20 moles) of 4-nitro-N-methyl phthalimide was added. The mixture was stirred overnight. Upon cooling to room temperature the product precipitated from solution. Filtration, washing the precipitate with water, and recrystallization from isopropanol yielded 50.8 grams of 4-(p-chlorophenyl)-N-methyl phthalimide. The melting point was 131°-132° C.

To a dry 250 ml. flask equipped with a magnetic stirring bar and nitrogen inlet were added 0.65 grams (C. 00502 moles) nickel chloride, 5.00 grams (0.01906 moles) triphenyl phosphine, 5.00 grams (0.0486 moles) sodium bromide, 7.51 grams (0.115 moles) zinc dust, and 2.88 grams (0.010 moles) 4-(p-chlorophenol)-N-methyl phthalimide. After purging with nitrogen for 60 minutes, 75 ml. of dry dimethylacetamide was added and the mixture was heated to 70° C. with stirring. After three hours the mixture was cooled, poured into water and filtered. This crude material was purified and separated from the inorganics by dissolving in hot chlorobenzene and filtering. Upon cooling, the product precipitated from solution. Filtration and drying (80° C. overnight) yielded 2.1 grams of bisimide. Mp 201°-203° C.

EXAMPLE II

To a dry 250 ml flask equipped with a magnetic stirring bar and nitrogen inlet were added 0.65 grams (0.00502 moles) nickel chloride, 3.75 grams (0.01906 moles) triphenyl phosphine, 5.00 grams (0.486 moles sodium bromide, 0.75 grams (0.0048 moles) dipyridyl, 7.51 grams (0.115 moles) zinc dust, and 25.0 grams (0.0869 moles) 4-(p-chlorophenol)-N-methyl phthalimide. This mixture was purged with nitrogen for 60 minutes and 75 ml of dry dimethylacetamide was added. The mixture was heated slowly to 70° C. After 5 hours the mixture was cooled, poured into water and filtered. The crude material was purified and separated from inorganics via dissolving in chlorobenzene and filtration. Upon cooling the product precipitated from solution. Filtration and drying overnight at 80° C. gave 32.7 grams of bisimide; Mp. 204°-205° C.

EXAMPLE III

The bisimides prepared in Examples I and II were converted to the corresponding dianhydride according to the following procedure.

In a 50 ml flast equipped with a reflux condenser and magnetic stirrer is added 3.2 grams of bisphenol bisimide, 3.0 grams of 50% aqueous sodium hydroxide, and 10 ml water. The mixture was heated at reflux for 18 hours, cooled to room temperature and acidified with an excess of 1N hydrochloric acid. The precipitated tetra acid was isolated by filtration, washed, and dried.

In a 50 ml flask equipped with a condenser thermometer and magnetic stirrer was charged 3.2 grams of tetra acid, 4.0 ml acetic anhydride, and 8.0 ml o-dichlorobenzene. The mixture was heated to 135° C. After 18 hours the solution was cooled. The dianhydride precipitates as a finely divided solid and is collected by filtration and washed with chilled hexane. The product was dried in vacuo at 60° C. overnight.

EXAMPLE IV

In a 100 ml flask equipped with Dean Stark trap/condenser, mechanical stirrer, nitrogen inlet and thermometer was added 2.90 g (0.00606 moles ) of the aforesaid dianhydride, 3.15 g (0.00605 moles) of BPA dianhydride (i.e. 2,2 bis (2,3-dicarboxyphenoxy phenyl) propone dianhydride), 1.31 g (0.121 moles) m-phenylene diamine, 0.03 g (0.00203 moles) phthalic anhydride, 35 ml m-cresol, 25 ml toluene. The mixture was heated under nitrogen at 100° C. for 30 minutes, followed by raising the temperature to 150° C. in which the water formed in the reaction was removed by azeotropic distillation. After about 4 hours the temperature was increased to 180° C. and held there for one hour, then cooled to room temperature. The viscous mixture was diluted with 100 ml of chloroform and the polymer isolated by precipitation in methanol. The precipitate was dried at 125° C. to give 6.6 grams of polyetherimide copolymer.

The polymer exhibited an intrinsic viscosity of 0.56 dl/gram when measured in phenol/tetrachloroethane (60/40; w/w), at 30° C. and a glass transition temperature of 230° C.

Obviously other modifications and variations of the present invention are possible in the light of the above teachings. It is, therefore, to be understood that changes may be made in the particular embodiments of the invention described which are within the full intended scope of the invention as defined by the appended claims.

I claim:

1. A process for the preparation of a copolymer having units of the formula:

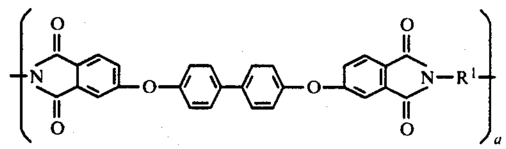

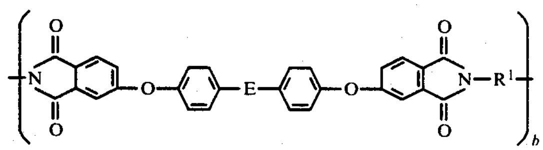

wherein a represents from 10 to 100 and b represents from 10 to 100; E is selected from phenylene, bisphenylene, naphthylene, alkylene or alkylidene, wherein $R^1$ is a divalent radical selected from the class consisting of (a) aromatic hydrocarbon radicals having from 6-20 carbon atoms and halogenated derivatives thereof, (b) alkylene radicals and cycloalkylene radicals having from 2-20 carbon atoms. $C_{2-8)}$ alkylene terminated polydiorganosiloxane, and (c) divalent readicals included by the formula:

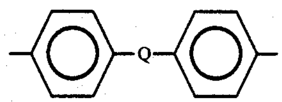

wherein Q is a member selected from the class consisting of —O—,

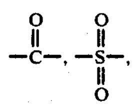

—S—, and —$C_2H_2$—, and x is a hole number from 1 to 5 inclusive, said process comprising (a) reacting a compound of the formula:

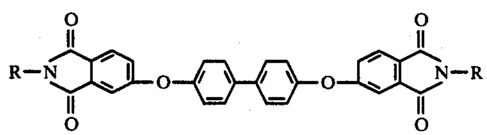

wherein R is lower alkyl of 1 to 6 carbons with alkali to form a tetraacid of the formula:

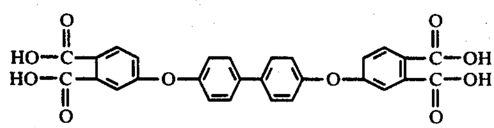

(b) dehydrating the tetraacid to a dianhydride;

(c) reacting a diamine of the formula $H_2N—R^1—NH_2$ wherein $R^1$ is the same as described hereinabove with a dianhydride

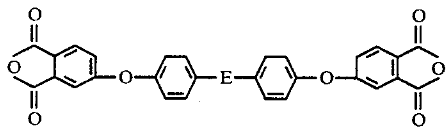

wherein E is the same as set forth hereinabove under polymer forming conditions to form the copolymer.

2. A process as defined in claim 1, wherein the diamine is phenylene diamine.

3. A process as defined in claim 2 wherein E is isopropylidene.

4. A copolymer having units of the formula:

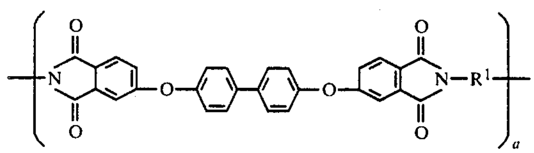

wherein $R^1$ is the residue of a divalent organic radical selected from the class consisting of (a) aromatic hydrocarbon radicals having from 6–20 carbon atoms and halogenated derivatives thereof, (b) alkylene radicals and cycloalkylene radicals having from 2–20 carbon atoms, $C_{(2-8)}$ alkylene terminated diorganosiloxane, and (c) divalent divalent radicals included by the formula:

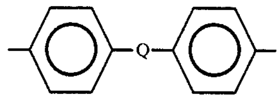

where Q is a member selected from the class consisting of —O—,

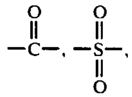

—S—, and —$C_2H_2$—, and x is a whole number from 1 to 5 inclusive, and a represents from 10 to 100; and units of the formula:

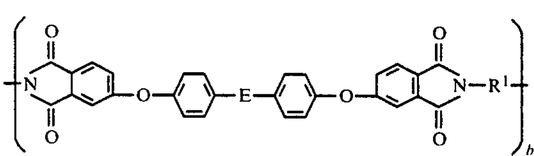

wherein B is selected from the group consisting of phenylene, bisphenylene, naphthylene, alkylene or alkylidene; and b is from 10 to 100, and $R^1$ is as defined above.

5. A copolymer as defined in claim 4 wherein $R^1$ is metaphenylene.

6. A copolymer as defined in claim 5 wherein E is isopropylidene.

* * * * *